United States Patent
Venkataraman et al.

(10) Patent No.: US 7,777,037 B2
(45) Date of Patent: Aug. 17, 2010

(54) ZIPRASIDONE PROCESS

(75) Inventors: Sundaram Venkataraman, Hyderabad (IN); Uppala Venkata Bhaskara Rao, Hyderabad (IN); Venkateswarlu Muvva, Hyderabad (IN); Vijayawardhan Chitta, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 983 days.

(21) Appl. No.: 11/259,321

(22) Filed: Oct. 26, 2005

(65) Prior Publication Data

US 2006/0089502 A1 Apr. 27, 2006

Related U.S. Application Data (60) Provisional application No. 60/630,757, filed on Nov. 24, 2004, provisional application No. 60/622,370, filed on Oct. 27, 2004.

(51) Int. Cl.
C07D 417/14 (2006.01)
(52) U.S. Cl. .................................................... 544/368
(58) Field of Classification Search ................. 544/368
See application file for complete search history.

(56) References Cited

U.S. PATENT DOCUMENTS

| | | | |
|---|---|---|---|
| 4,831,031 A | 5/1989 | Lowe, III et al. |
| 5,206,366 A | 4/1993 | Bowles |
| 5,312,925 A | 5/1994 | Allen et al. |
| 5,338,846 A | 8/1994 | Busch et al. |
| 5,359,068 A | 10/1994 | Urban |
| 6,110,918 A | 8/2000 | Busch et al. |
| 6,111,105 A | 8/2000 | Fox et al. |
| 6,245,765 B1 | 6/2001 | Busch et al. |

*Primary Examiner*—James O. Wilson
*Assistant Examiner*—Paul V. Ward
(74) *Attorney, Agent, or Firm*—Robert A. Franks; Lee C. Banks; Anjum Swaroop (57) ABSTRACT

A process for preparing ziprasidone having low levels of keto ziprasidone and hydroxy ziprasidone impurities.

19 Claims, 4 Drawing Sheets

ZIPRASIDONE PROCESS

CROSS-REFERENCE TO RELATED APPLICATIONS

This application is a nonprovisional filing of U.S. Provisional Application Nos. 60/622,370 filed on Oct. 27, 2004 and 60/630,757 filed on Nov. 24, 2004, the entire disclosures of which are hereby incorporated by reference.

INTRODUCTION TO THE INVENTION

The present invention relates to preparing ziprasidone having low concentrations of impurities. Ziprasidone has the chemical name 5-[2-[4-(1,2-benzisothiazol-3-yl)-1-piperazinyl]ethyl]-6-chloro-1,3-dihydro-2H-indol-2-one and is represented structurally by Formula I.

Formula I

Ziprasidone is useful as an antipsychotic agent and is used for treating various mental disorders including schizophrenia. It is commercially available in products sold under the brand name GEODON™, as capsules containing ziprasidone hydrochloride monohydrate and in a lyophilized form of ziprasidone mesylate trihydrate, for reconstitution and injection.

U.S. Pat. No. 4,831,031 describes ziprasidone, its related compounds and their syntheses.

A method for specifically synthesizing ziprasidone hydrochloride monohydrate is described in U.S. Pat. No. 5,312,925.

A method for synthesizing ziprasidone mesylate dihydrate is described in U.S. Pat. No. 6,245,765; and a method for synthesizing ziprasidone mesylate trihydrate is described in U.S. Pat. No. 6,110,918.

U.S. Pat. Nos. 5,338,846; 5,359,068; and 6,111,105 also describe methods for synthesizing ziprasidone and intermediates thereof.

U.S. Pat. No. 5,206,366 describes a process for synthesizing ziprasidone, in 94.5% purity, by condensing 2-chloroethyl-6-chlorooxindole with 3-piperazinyl-1,2-benzisothiazole in aqueous sodium carbonate, to form the ziprasidone base. The base was then converted to the hydrochloride salt. The starting 2-chloroethyl-6-chlorooxindole compound could have been prepared as in steps A and B of example 12 in U.S. Pat. No. 4,831,031.

Referring to reaction Scheme 1, the reduction of 5-(2-chloroacetyl)-6-chloro-2-oxindole of Formula IV using triethylsilane and a strong acid would be expected to result in a mixture of 5-(2-chloroethyl)-6-chloro oxindole of Formula V, 5-(2-Chloroacetyl)-6-chloro-2-oxindole of Formula IV (residual unreacted material), and 5-(2-chlorohydroxl ethyl)-6-chloro oxindole of Formula IVa. These compounds, upon condensation with 3-(1-piperazinyl)-1,2-benzisothiazole of Formula VI, lead to the formation of ziprasidone of Formula I containing the impurities: keto ziprasidone, which is described chemically as 5-(2-(4-(1,2-benzisothiazole-3-yl) 1-piperazinyl)-1-oxoethyl)-6-chloro-1,3-dihydro-2H-indole-2-one (Formula Ia); and hydroxy ziprasidone which is described chemically as 5-(2-(4-(1,2-benzisothiazole-3-yl) 1-piperazinyl)-1-hydroxy ethyl)-6-chloro-1,3-dihydro-2H-indole-2-one (Formula Ib). This is shown in reaction Scheme 1.

Scheme 1

-continued

There remains a need for a method of synthesis of ziprasidone and ziprasidone hydrochloride substantially free from the keto ziprasidone and hydroxy ziprasidone impurities.

There is also a need for purifying ziprasidone to remove the keto ziprasidone and hydroxy ziprasidone impurities.

These and other embodiments comprise aspects of this invention.

SUMMARY OF THE INVENTION

One aspect of the present invention provides a ziprasidone composition substantially free from the hydroxy ziprasidone and keto ziprasidone impurities.

In another aspect, the invention provides a process for the preparation of ziprasidone comprising not greater than about 1500 ppm of the hydroxy ziprasidone or about 1000 ppm of the keto ziprasidone impurities.

A ziprasidone composition comprising an amount of keto ziprasidone and hydroxy ziprasidone of not greater than about 1500 ppm or about 1000 ppm can be prepared by a process comprising the steps of:

a) acylating 6-chloro-1,3-dihydro-2H-indol-2-one of Formula III with chloroacetyl chloride by a Friedel-Crafts acylation to synthesize 5-(2-chloroacetyl)-6-chloro-2-oxindole of Formula IV;

Formula III

Formula IV b) reducing the compound of Formula IV with an excess of triethylsilane in the presence of a strong acid to form a product comprising a mixture of 5-(2-chloroethyl)-6-chlorooxindole of Formula V, the 5-(2-chloroacetyl)-6-chloro-2-oxindole impurity of Formula IV, and the 5-(2-chlorohydroxylethyl)-6-chlorooxindole of Formula IVa;

Formula V

Formula IVa c) condensing the mixture obtained in step b) with 3-(1-piperazinyl)-1,2-benzisothiazole of Formula VI to form crude ziprasidone of Formula I, containing the keto ziprasidone impurity of Formula Ia and the hydroxy ziprasidone impurity of Formula Ib;

d) purifying the crude ziprasidone by slurrying or recrystallization or a combination thereof to remove the keto and hydroxy ziprasidone impurities; and e) converting ziprasidone to ziprasidone hydrochloride, followed by any desired subsequent purification.

A further aspect of the invention provides the compound 5-(2-(4-(1,2-benzisothiazole-3-yl)-1-piperazinyl)-1-oxoethyl)-6-chloro-1,3-dihydro-2H-indole-2-one of Formula Ia (referred to herein as "keto ziprasidone impurity").

In a further aspect of the invention there is provided a process for the preparation of the keto ziprasidone impurity of Formula Ia comprising the steps of:

a) refluxing a mixture of 3-(1-piperazinyl)-1,2-benzisothiazole of Formula VI and 5-(2-Chloroacetyl)-6-chloro-2-oxindole of Formula IV in the presence of a solvent, a suitable base, an alkali halide and t-butyl ammonium bromide to obtain the crude keto ziprasidone impurity;

b) purifying the crude keto ziprasidone impurity by slurrying, recrystallization, or a combination thereof; and c) optionally, converting the compound obtained in step b) into its hydrochloride salt.

The process is depicted in reaction Scheme 2, as follows:

In yet another aspect of the invention, there is provided a process for the preparation of the hydroxy impurity of ziprasidone of Formula Ib comprising:

a) refluxing a mixture of 3-(1-piperazinyl)-1,2-benzisothiazole of Formula VI and 5-(2-chlorohydroxylethyl)-6-chlorooxindole of Formula IVa in the presence of a solvent, a suitable base, and an alkali halide to give the crude hydroxy ziprasidone impurity of Formula Ib.

b) purifying the crude hydroxy ziprasidone impurity obtained above by slurrying, recrystallization, or a combination thereof; and c) optionally, converting the compound obtained in step b) into its hydrochloride salt.

The process is depicted in reaction Scheme 3, as follows:

The ziprasidone hydrochloride obtained by the processes of the invention are substantially free of the keto ziprasidone and the hydroxy ziprasidone impurities.

DETAILED DESCRIPTION

Figure 1:
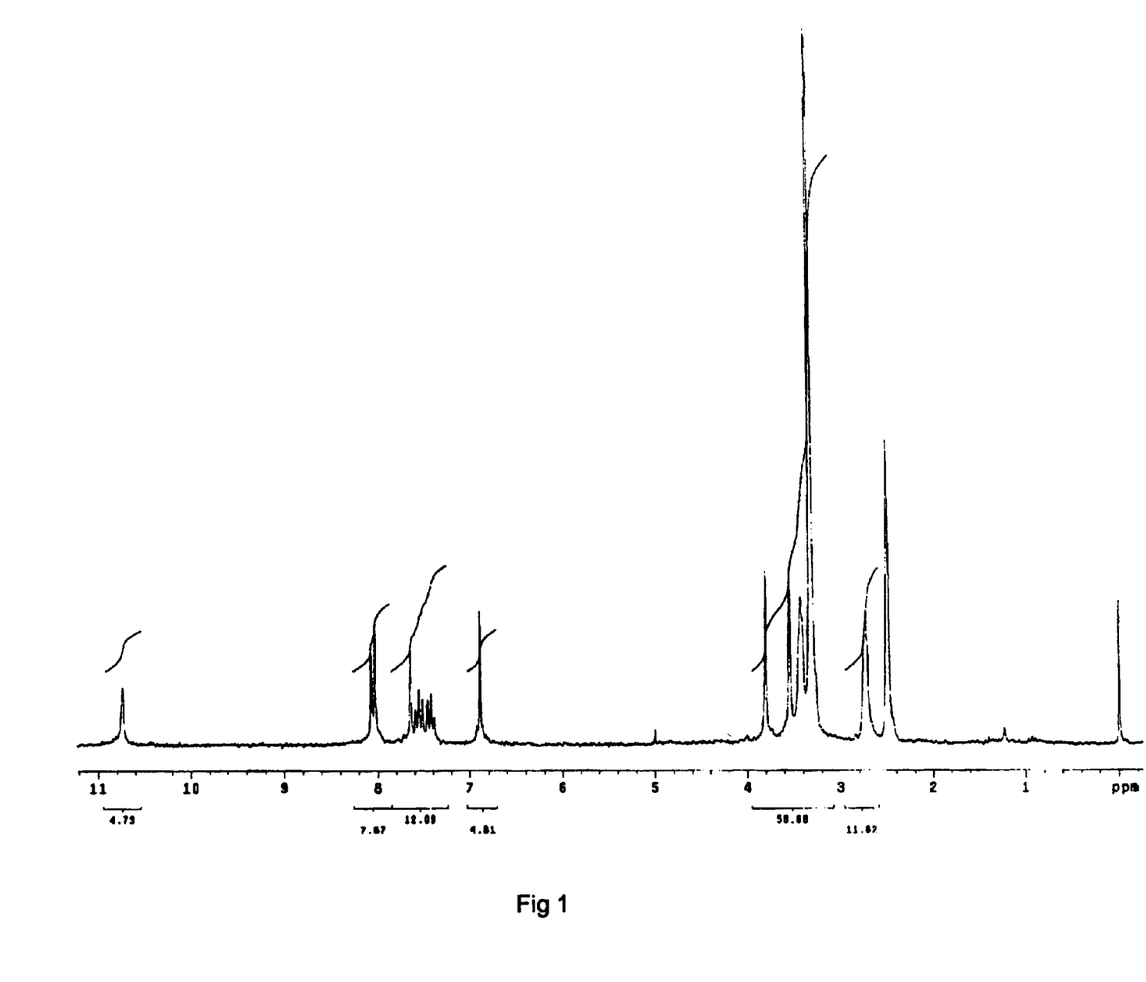
FIG. 1 is a $^1$H-NMR of the compound of Formula (Ia).
Figure 2:
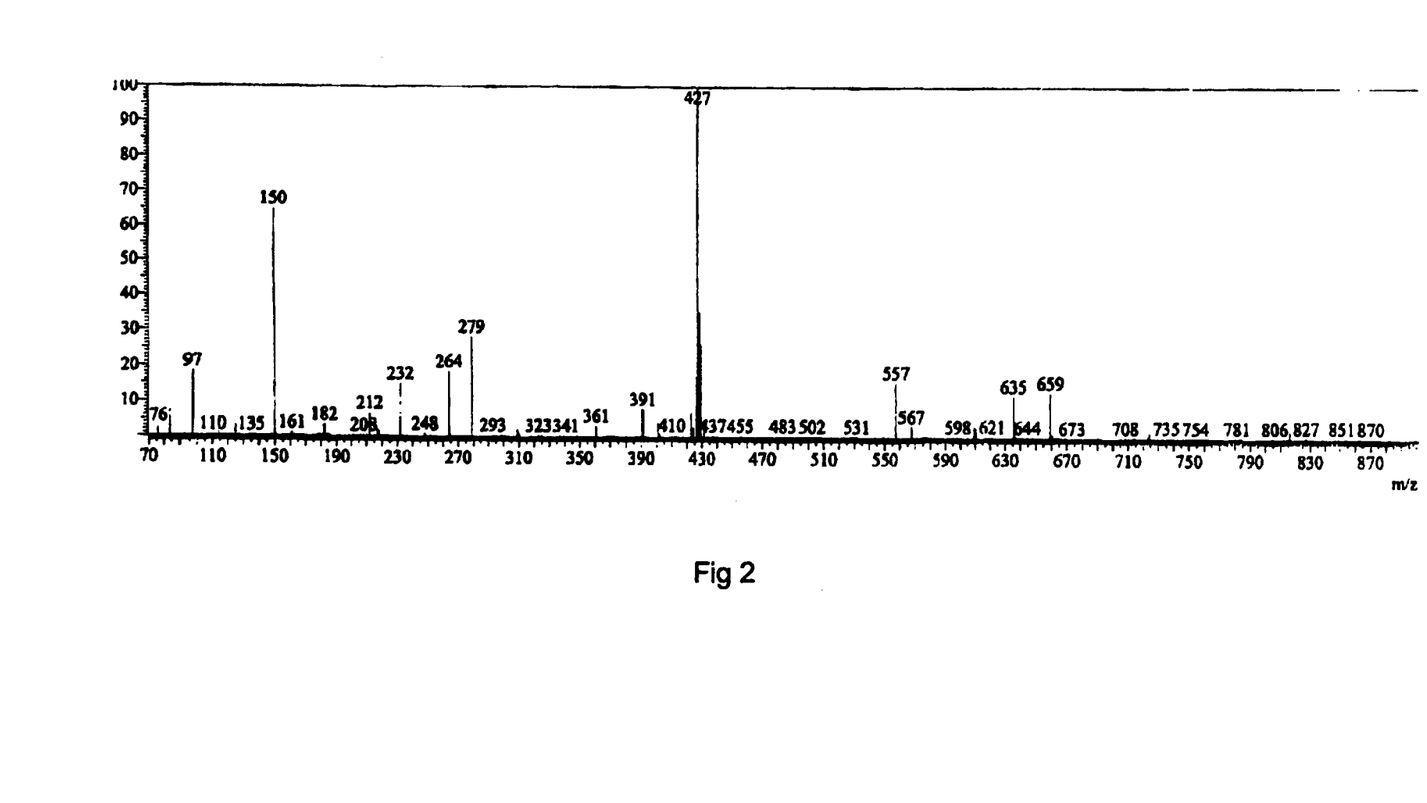
FIG. 2 is a mass spectrum of the compound of Formula (Ia).
Figure 3:
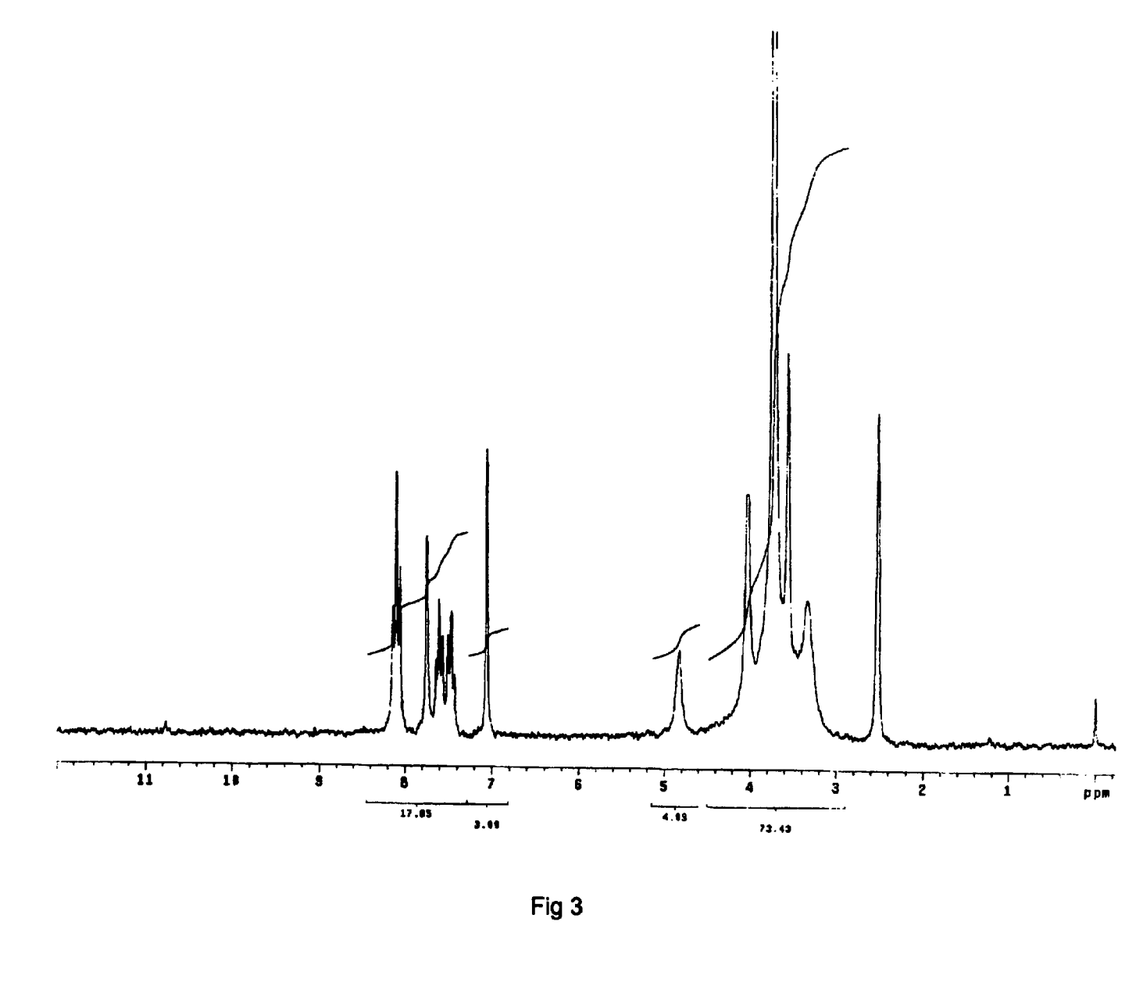
FIG. 3 is a $^1$H-NMR of the compound of Formula (Ib).
Figure 4:
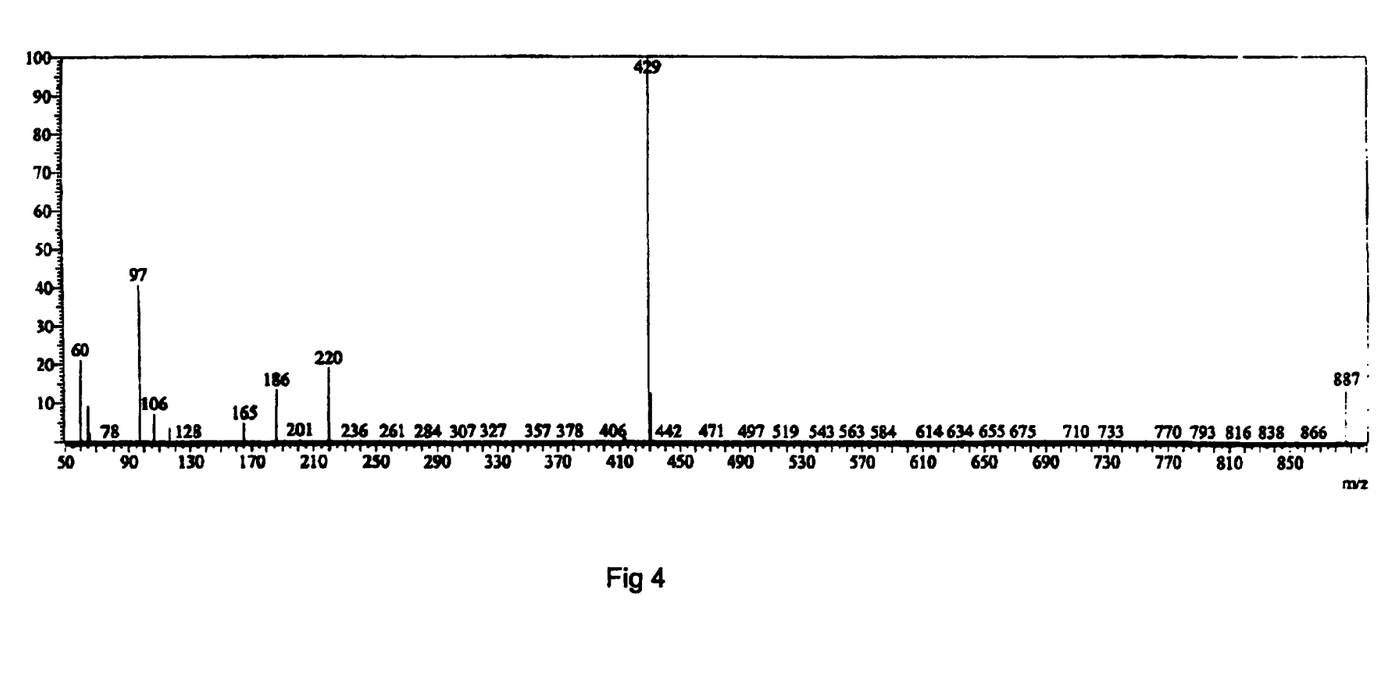
FIG. 4 is a mass spectrum of the compound of Formula (Ib).

An aspect of the present invention provides ziprasidone, substantially free from hydroxy ziprasidone and keto ziprasidone impurities.

"Ziprasidone" as described herein is intended to mean ziprasidone base or any of its salts.

In one aspect, the invention provides a process for the preparation of ziprasidone comprising not greater than about 1500 ppm of the hydroxy ziprasidone or about 1000 ppm of the keto ziprasidone impurities.

In an embodiment, ziprasidone comprising keto and hydroxy ziprasidone impurities no greater than about 1500 ppm, or about 1000 ppm can be prepared by a process comprising the steps of:

a) acylating 6-chloro-1,3-dihydro-2H-indol-2-one of Formula III with chloroacetyl chloride by Friedel-Crafts acylation to synthesize 5-(2-chloroacetyl)-6-chloro-2-oxindole of Formula IV;

Formula III

Formula IV b) reducing the compound of Formula IV with an excess of triethylsilane in the presence of a strong acid to form a product comprising a mixture of 5-(2-chloroethyl)-6-chlorooxindole of Formula V, the 5-(2-chloroacetyl)-6-chloro-2-oxindole impurity of formula IV, and the 5-(2-chlorohydroxylethyl)-6-chlorooxindole of Formula IVa;

Formula V

Formula IVa c) condensing the mixture with 3-(1-piperazinyl)-1,2-benzisothiazole of Formula VI to form crude ziprasidone of Formula I, containing the keto ziprasidone impurity of Formula Ia and the hydroxy ziprasidone impurity of Formula Ib;

VI

Formula Ia

Formula Ib d) purifying the crude ziprasidone by slurrying, recrystallization, or a combination thereof to remove the keto and hydroxy ziprasidone impurities; and e) converting the ziprasidone to ziprasidone hydrochloride, followed by desired subsequent purification.

Step a) involves acylation of a composition comprising 6-chloro-1,3-dihydro-2H-indol-2-one of Formula III with chloroacetyl chloride by Friedel-Crafts acylation to obtain 5-(2-chloroacetyl)-6-chloro-2-oxindole of Formula IV.

Suitable solvents for the reaction include but are not limited to $C_1$-$C_6$ straight chain or branched chloro hydrocarbons such as dichloromethane, ethylene dichloride, chloroform, carbon tetrachloride, chloro benzene, dichlorobenzene, and the like; and mixtures thereof.

Step b) involves reducing the compound of Formula IV with an excess of triethylsilane in the presence of a strong acid to form a product comprising a mixture of 5-(2-chloroethyl)-6-chloro oxindole of Formula V, 5-(2-chloroacetyl)-6-chloro-2-oxindole of Formula IV and 5-(2-chlorohydroxylethyl)-6-chloro oxindole of Formula Iva. The excess of triethylslane comprises about 2.4 to 2.5 equivalents of the triethylsilane with respect to the starting material, 5-(2-chloroacetyl)-6-chloro-2-oxindole of Formula IV.

Suitable strong acids which can be used for the above reaction include but are not limited to trifluoroacetic acid, methanesulphonic acid, polyphosphoric acid and the like. Other strong acids can also be used in this reaction either alone or in combination with the acids mentioned above, and are all included herein without limitation.

Step c) involves condensing the mixture with 3-(1-piperazinyl)-1,2-benzisothiazole of Formula VI to form crude ziprasidone of Formula I, containing the keto ziprasidone impurity of Formula Ia and the hydroxy ziprasidone impurity of Formula Ib.

Step d) involves purifying the crude ziprasidone to remove the keto and hydroxy ziprasidone impurities.

The purification of ziprasidone crude can be achieved by recrystallization, reslurrying or a combination thereof, typically followed by drying of the resultant wet compound.

The recrystallization and/or reslurrying are conducted in a suitable solvent or mixture of solvents, such as: $C_1$-$C_5$ alcohols like methanol, ethanol, butanol, tertiary butyl alcohol, and the like; halogenated solvents such as dichloromethane, carbon tetrachloride, chloroform, and the like; or mixtures thereof.

The recrystallization and/or slurrying is performed optionally accompanied by stirring. Any conventional means of stirring is acceptable as known to a person skilled in the art.

The crystallization step can be performed by initially attaining the dissolution of ziprasidone, typically at elevated temperatures of about 50 to 90° C., or about 60 to 70° C., to maximize the solute concentration. The heating may be optionally accompanied by stirring.

Crystallization of the compound can be attained at about 20 to 25° C. or at any temperatures lower than that used to form the solution, for example, about 0° C. to 10° C. The crystallization step may further include cooling the solution, heating the solution, or adding a seeding agent to induce precipitation.

For the optional seeding, crystals of the desired product are added to a solution, prior to initiating crystallization. For example, about 1 to 20 percent by weight of ziprasidone crystals can be added as cooling is commenced.

The crystalline material obtained as described above is typically further subjected to drying. Drying can be performed under reduced pressure or under atmospheric pressure at a temperature of at least about 40° C. to 90° C., or 70 to 80° C., or higher, for sufficient time to achieve the desired residual solvent content, for example about 1 to 3 days. Any conventional method of drying such as for example vacuum tray drying, fluid bed drying, tray drying, and the like may be used and are all within the scope of this invention.

Step e) involves converting the ziprasidone to ziprasidone hydrochloride, followed by desired purification.

Suitable solvents useful for the conversion of the ziprasidone to ziprasidone hydrochloride include but are not limited to $C_1$ to $C_5$ straight chain carboxylic acids, ethyl acetate, toluene, $C_1$ to $C_5$ alcohols, halogenated solvents, and mixtures thereof.

Suitable solvents in which ziprasidone hydrochloride can be dissolved before purification include but are not limited to dimethylformamide, tetrahydrofuran, $C_1$ to $C_5$ straight chain carboxylic acids, and the like. The concentration of the ziprasidone hydrochloride in the solvent can range from 40 to 80% or more. The solution can be prepared at an elevated temperature if desired to achieve the desired concentration. Any temperature is acceptable for the dissolution as long as a clear solution of the ziprasidone hydrochloride is obtained and is not detrimental to the drug substance chemically or physically. The solution may be brought down to room temperature for further processing if required or an elevated temperature may be used. A higher temperature will allow the precipitation from solutions with higher concentrations of ziprasidone hydrochloride resulting in better economies of manufacture.

For crystallizing ziprasidone hydrochloride, crystals of the desired product can optionally be added to a solution, prior to initiating crystallization. For example, about 1 to 20 percent by weight of ziprasidone hydrochloride crystals can be added as cooling is commenced.

Where antisolvents are used for precipitation, suitable antisolvents for precipitation of the ziprasidone hydrochloride from solution include but are not limited to cyclohexane, ethyl acetate, n-heptane, n-hexane, toluene, and the like. The ratio of solvent to the antisolvent can range from 1:2 to 1:10.

A further aspect of the invention provides a compound 5-(2-(4-(1,2-benzisothiazole-3-yl)-1-piperazinyl)-1-oxoethyl)-6-chloro-1,3-dihydro-2H-indole-2-one (keto ziprasidone impurity) of Formula Ia.

In another aspect of the invention there is provided a process for the preparation of the keto impurity of ziprasidone of Formula Ia, comprising the steps of:

a) refluxing a mixture of 3-(1-piperazinyl)-1,2-benzisothiazole of Formula VI, 5-(2-Chloroacetyl)-6-chloro-2-oxindole of Formula IV, a solvent, a base, an alkali metal halide and t-butyl ammonium bromide to obtain the crude keto ziprasidone impurity;

b) purifying the above obtained compound by slurrying, recrystallization, or a combination thereof; and c) optionally, converting the compound into its hydrochloride salt.

Suitable solvents for the reaction of step a) include but are not limited to $C_1$-$C_8$ straight chain, branched chain, or cyclic hydrocarbons such as toluene, cyclohexane, n-heptane, n-hexane, and the like. Suitable bases which can be used include but are not limited to alkali metal hydroxides, carbonates and bicarbonates like sodium carbonate, sodium hydroxide, potassium carbonate, sodium bicarbonate, and the like. Alkali metal halides which can be used include but are not limited to sodium iodide and potassium iodide.

The mixture containing the keto ziprasidone impurity can be purified by recrystallization and/or reslurrying in a suitable solvent or mixture of solvents, such as for example: $C_1$-$C_5$ alcohols like methanol, ethanol, butanol, tertiary butyl alcohol, etc.; halogenated solvents like dichloromethane, carbon tetrachloride, and chloroform; or mixtures thereof.

In yet another aspect of the invention, there is provided a process for the preparation of the hydroxy impurity of ziprasidone of Formula Ib comprising the steps of:

a) refluxing a mixture of 3-(1-piperazinyl)-1,2-benzisothiazole of Formula VI, 5-(2-chlorohydroxylethyl)-6-chloro oxindole of Formula IVa, a base, and an alkali metal halide in water to give the crude hydroxy ziprasidone impurity of Formula Ib;

b) purifying the compound obtained above by slurrying, recrystallization, or a combination thereof; and c) optionally, converting the compound into its hydrochloride salt.

Suitable solvents for the reaction of step a) include polar solvents like alcohols such as methanol, ethanol, butanol, water or mixtures thereof. Suitable bases which can be used include alkali metal hydroxides, carbonates and bicarbonates like sodium carbonate, sodium hydroxide, potassium carbonate, sodium bicarbonate and the like. Alkali metal halides which can be used include but are not limited to sodium iodide, and potassium iodide.

The compound obtained in step b) can be further purified by recrystallization and/or reslurrying in a suitable solvent or mixture of solvents such as: $C_1$-$C_5$ alcohols like methanol, ethanol, butanol, tertiary butyl alcohol and the like; halogenated solvents like dichloromethane, carbon tetrachloride, and chloroform; or mixtures thereof.

Any of the solutions of ziprasidone or ziprasidone hydrochloride or the active ingredients along with either the keto ziprasidone or hydroxy ziprasidone impurities as described in the foregoing descriptions can be prepared at an elevated temperature if desired to achieve complete solubilization.

Any temperature is acceptable for the dissolution as long as a clear solution of the ziprasidone hydrochloride is obtained and is not detrimental to the drug substance chemically or physically. The solution may be brought down to room temperature for further processing if required or elevated temperature may be used. A higher temperature will allow the preparation of solutions with higher concentrations of ziprasidone hydrochloride resulting in better economies of manufacture.

The appropriate choice of the temperatures and the concentrations of the different compositions in the solvents chosen for the reactions will be within the scope of understanding of a person skilled in the art.

Ziprasidone prepared according to this embodiment is substantially free from the keto ziprasidone and hydroxy ziprasidone impurities. The level of the keto ziprasidone and the hydroxy ziprasidone impurities can be determined by high performance liquid chromatography ("HPLC") or other analytical methods without limitation. The ziprasidone drug substance of the invention contains not more than about 1000 ppm, or 750 ppm, or 500 ppm, or 250 ppm, or 100 ppm of the keto ziprasidone impurity. The ziprasidone drug substance of the invention contains not more than about 1500 ppm, or 1000 ppm, or 750 ppm, or 500 ppm, or 250 ppm, or 100 ppm of the hydroxy ziprasidone impurity. The impurities can each be in the free base form, or as a salt, such as the hydrochloride or mesylate.

In one embodiment, the ziprasidone drug substance of the present invention is ziprasidone free base. In another embodiment, the ziprasidone drug substance of the present invention is ziprasidone hydrochloride anhydrous, or ziprasidone hydrochloride monohydrate, or hemihydrate. In another embodiment, the ziprasidone drug substance is ziprasidone mesylate dihydrate, and in another embodiment, the ziprasidone drug substance is ziprasidone mesylate trihydrate.

The term "ziprasidone drug substance", as used herein and unless otherwise indicated, refers to ziprasidone or a salt thereof, as defined above. The ziprasidone drug substance of the present invention finds use in the preparation of pharmaceutical formulations such as for example tablets, capsules, granules, powders, and the like for use in the treatment of various disease conditions. Such pharmaceutical formulations can contain, as required, pharmaceutical carriers, excipients, flavorings, and other ingredients that are used in the preparation of pharmaceutical formulations as known in the art.

The following examples illustrate certain specific aspects and embodiments of the present invention in greater detail, and are not intended to limit the scope of the invention.

EXAMPLE 1

Synthesis of 5-[2-[4-(1,2benzisothiozol-3-yl)-1-piperazinyl]-ethyl]-6-chloro-1,3-dihydro-2H-indol-2-one (Ziprasidone, Formula I)

Step 1: Preparation of 3-(1-piperazinyl)-1,2-benzisothiazole (Formula VI)

A mixture of 508.2 g of piperazine, 200 ml of tertiary butanol and 200 g of 3-chloro-1,2-benzisithiazole was refluxed for 15 hours. The reaction mass was quenched with 800 ml of water and filtered through a Hyflow (flux calcined diatomaceous earth) bed to make it particle-free. The pH of the reaction mass was adjusted to 13 with 50% aqueous NaOH and then the reaction mass was extracted three times with 1200 ml volumes of toluene. The combined organic layers were washed with 200 ml of water, treated with 10 g of carbon, and the carbon was removed by filtration. The solvent was distilled until about 1000 ml remained, under reduced pressure at a temperature below 65° C. The reaction mass was cooled to 0-5° C. and stirred for 80 minutes. The formed solid was filtered and washed with 20 ml of toluene to yield 148.3 g of the title compound.

Step 2: Preparation of 5-(2-chloro acetyl)-6-chloro oxindole (Formula IV)

A mixture of 750 ml of dichloromethane, 150 g of 6-chlorooxindole, 161.6 g of chloroacetyl chloride and 477.2 g of aluminium chloride was refluxed for 9.5 hours. The reaction mass was quenched into a mixture of crushed ice and 135 ml of hydrochloric acid. The formed solid was filtered, and the wet compound was washed with water. The wet compound was dissolved in 3525 ml acetic acid by heating to 70 to 80° C., then carbon was added and the mixture was stirred briefly at the same temperature, and the carbon was removed by filtration and washed with 15 ml of acetic acid. The filtrate was allowed to cool to about 20° C. for solid formation. The solid was filtered, washed three times with 600 ml of water, and then dried to yield 148.5 g of the title compound.

Step 3: Preparation of 5-(2-chloro ethyl)-6-chlorooxindole (Formula V)

A mixture of 130 g of 5-(2-chloroacetyl)-6-chlorooxindole, 455 ml of trifluoroacetic acid and 148.6 g of triethylsilane was maintained at a temperature of about 40-45° C. for 7 hours. The reaction mass was filtered at −5 to 0° C. after maintaining for 1 to 2 hours at the same temperature. The compound was washed with 130 ml of water and further slurried in 650 ml of water. After separation from the water, it was then dried to yield 113 g of the title compound.

Step 4: Preparation of Crude Ziprasidone Base (Formula I)

A mixture of 100 g of 5-(2-chloroethyl)-6-chlorooxindole, 95.2 g of 3-(1-piperazinyl)-1,2-benzisothiazole, 92.1 g of sodium carbonate, 6.5 g of sodium iodide, 28 g of tetrabutylammonium bromide and 1000 ml of cyclohexane was refluxed until reaction completion as shown by thin layer chromatography. The reaction mass was cooled to 30° C. and the solid was filtered. 1000 ml of water was added to the wet compound and stirred for 95 minutes. The solid was filtered and washed with 100 ml water. To the wet compound, 1000 ml methanol was added and stirred for 2.5 to 3 hours at room temperature. The compound was filtered and washed with 200 ml of methanol and dried to afford 142.6 g of the title compound.

Step 5: Purification of Ziprasidone Base (Formula I)

120 g of crude ziprasidone base, 750 ml of methanol, and 2250 ml of chloroform were heated to reflux until a clear solution was obtained. 6 g of carbon was added to the resulting reaction solution and maintained at reflux temperature for 20 minutes. The carbon was removed by filtration and the filtrate was heated to distill the solvent until about 1160 ml of distillate was collected. 1200 ml of methanol was added slowly to the reaction mass and the mixture was cooled to a temperature of 30° C. and stirred at the same temperature for 1.5 to 2 hours. Then the formed solid was filtered, washed with 240 ml methanol and dried to afford 89.3 g of the title compound substantially free of the keto ziprasidone (about 80 ppm by HPLC) and hydroxy ziprasidone (about 30 ppm by HPLC) impurities.

EXAMPLE 2

Preparation of Ziprasidone Hydrochloride (Formula II)

75 g of pure ziprasidone base was dissolved in 225 ml of glacial acetic acid at 30° C. 0.75 g of carbon was added to the resulting reaction solution and stirred for 10 minutes at the same temperature. The carbon was filtered and the carbon bed was washed with 7.5 ml of acetic acid. Then the filtrate was added slowly to a mixture of 450 ml ethyl acetate and 99 ml ethyl acetate-hydrochloride (assay 10.57% HCl w/v) at a temperature of 30° C. for 60 min. The reaction mixture was stirred for 1 hour 50 min at the same temperature. The compound was filtered and washed with 185 ml ethyl acetate and dried at a temperature of 90 to 100° C. to afford 80 g of the title compound.

EXAMPLE 3

Crystallization of Ziprasidone Hydrochloride (Formula II)

70 g of ziprasidone hydrochloride and 105 ml of 99-100% formic acid was heated to 60-65° C. for clear dissolution. The reaction mass was filtered and washed with 7 ml of formic acid. The filtrate was cooled to 50-55° C. and seed ziprasidone hydrochloride was added and stirred for 1 hour and 45 minutes at 50-55° C. The reaction mass was cooled slowly to 25-35° C. in 50 minutes. 315 ml of ethyl acetate was added slowly at 25-35° C. over 2 hours and stirred for 90 minutes at 25-35° C. The compound was filtered under a nitrogen atmosphere and 234 ml of glacial acetic acid was added at 25-35° C. under stirring over 50 minutes at 25-35° C. The compound was filtered under a nitrogen atmosphere and washed with 116 ml of ethyl acetate. The compound was dried to get 58.7 g of the title compound, substantially free of the keto ziprasidone (about 90 ppm by HPLC) and hydroxy ziprasidone (about 40 ppm by HPLC) impurities.

EXAMPLE 4

Preparation of 5-(2-(4-(1,2-benzisothiozole-3-yl)1-piperazinyl)-1-oxoethyl)-6-chloro-1,3-dihydro-2H-indole-2-one (Formula Ia)

8.9 g of 3-(1-piperazinyl)-1,2-benzisothiazole, 10 g of 5-(2-chloroacetyl)-6-chlorooxindole, 100 ml cyclohexane, 8.48 g of sodium carbonate, 0.6 g of sodium iodide, and 2.6 g of t-butyl ammonium bromide were placed into a round bottom flask and heated to reflux. The reaction mixture was refluxed for 30 to 35 hours. The reaction mass was cooled to 25-35° C. and checked for reaction completion using thin layer chromatography. After reaction completion, 50 ml of water was added to the reaction mass and stirred for 15 to 20 minutes at 25-35° C. The solid was filtered and washed with 10 ml of water. 100 ml of water was added to the wet solid and stirred for 1 to 2 hours at 25-35° C. The solid was filtered and washed with 10 ml of water. 100 ml of methanol was added to the wet solid and stirred for 2 to 3 hours at 25-35° C. The solid was filtered and washed with 10 ml of methanol and dried to get 9.2 g of the title compound.
Purity by HPLC: 96.8%.
MS(%) M$^{+1}$ 426+1.
NMR (d, CDCl$_3$): 3.2-3.6 (m, 8H), 7.4-7.7 (m, 2H), 7.8 (d, 1H), 7.87 (d, 1H), 2.7 (s, 2H), 6.9 (s, 1H), 10.8 (s, 1H), 3.8 (s, 2H), 7.7 (s, 1H).

EXAMPLE 5

Purification of 5-(2-(4-(1,2-benzisothiozole-3-yl) 1-piperazinyl)-1-oxoethyl)-6-chloro-1,3-dihydro-2H-indole-2-one (Formula Ia)

4.0 g of 5-(2-(4-(1,2-benzisothiozole-3-yl) 1-piperazinyl)-1-oxoethyl)-6-chloro-1,3-dihydro-2H-indole-2-one (Ia) and 40 ml of methanol was added into a round bottom flask and stirred for 50 to 60 minutes at 25-35° C. The compound was filtered and washed with 8 ml of methanol. The compound was dried to afford 3.4 g of the title compound.

EXAMPLE 6

Preparation of 5-(2-(4-(1,2-benzisothiozole-3-yl)-1-piperazinyl)-1-oxoethyl)-6-chloro-1,3-dihydro-2H-indole-2-one Hydrochloride 1.0 g of 5-(2-(4-(1,2-benzisothiozole-3-yl)-1-piperazinyl)-1-oxoethyl)-6-chloro-1,3-dihydro-2H-indole-2-one of Formula Ia and 10 ml of water was added into a round bottom flask and stirred for 10 to 15 minutes. The pH of the mixture was adjusted to approximately 2 with hydrochloric acid. The reaction mass was maintained for 45 to 60 minutes at 25-35° C. The compound was filtered and washed with 20 ml of water and dried to afford 1.0 g of the title compound.

EXAMPLE 7

Preparation of 5-(2-(4-(1,2-benzisothiozole-3-yl)-1-piperazinyl)-1-hydroxyethyl)-6-chloro-1,3-dihydro-2H-indole-2-one (Formula Ib)

16 g of 3-(1-piperazinyl)-1,2-benzisothiazole, 20 g of 5-(2-chlorohydroxyethyl)-6-chlorooxindole of Formula IVa, 22.4 g of potassium carbonate, 2.7 g of potassium iodide, and 200 ml of water were taken into a round bottom flask. The reaction mass was stirred and heated to reflux. The reaction mass was maintained under reflux for 13 to 15 hours. The reaction mass was cooled to 25-35° C. and the supernatant water was decanted from the reaction mass. 100 ml acetone was added to the above reaction mass and stirred for 30 to 45 minutes. The solid was filtered and washed with 20 ml of acetone. The solid was dried to yield 7.3 g of the title compound.
Purity by HPLC: 93.04%.
MS(%) M$^{+1}$ 428+1.
NMR D$_2$O exchange (d, CDCl$_3$): 3.2-3.8 (m, 8H), 2.5 (s, 2H), 4.1 (s, 2H), 7.4-7.7 (m, 2H), 8.1 (s, 1H), 2.5 (s, 2H), 4.8 (s, 1H), 4.1 (s, 2H), 7.7 (s, 1H).

EXAMPLE 8

Preparation of 5-(2-(4-(1,2-benzisothiozole-3-yl)-1-piperazinyl)-1-hydroxyethyl)-6-chloro-1,3-dihydro-2H-indole-2-one Hydrochloride 6.5 g of 5-(2-(4-(1,2-benzisothiozole-3-yl)-1-piperazinyl)-1-hydroxyethyl)-6-chloro-1,3-dihydro-2H-indole-2-one of Formula Ib and 65 ml water was charged into a round bottom flask and stirred for 5 to 10 minutes. The pH of the mixture was adjusted to approximately 2 with hydrochloric acid and maintained for 5 to 10 minutes. The compound was filtered and washed with 100 ml of water and dried to get 5.7 g of the pure title compound.

We claim:

1. A process for preparing ziprasidone or a salt thereof, comprising:
   condensing a mixture comprising 5-(2-chloroethyl)-6-chlorooxindole, 5-(2-chloroacetyl)-6-chloro-2-oxindole, and 5-(2-chlorohydroxylethyl)-6-chlorooxindole with 3-(1-piperazinyl)-1,2-benzisothiazole to form a mixture of ziprasidone and impurities; and
   purifying the ziprasidone by slurrying, recrystallization, or a combination thereof.

2. The process of claim 1, wherein purifying comprises combining a mixture of ziprasidone and impurities with a solvent.

3. The process of claim 2, wherein a solvent comprises a $C_1$-$C_5$ alcohol, a halogenated solvent, or a mixture thereof.

4. The process of claim 1, wherein ziprasidone or a salt thereof contains not greater than about 1500 ppm of a hydroxy ziprasidone impurity and not greater than about 1000 ppm of a keto ziprasidone impurity.

5. The process of claim 1, wherein purifying comprises:
   1) dissolving impure ziprasidone in a mixture of a $C_1$-$C_5$ alcohol and a halogenated solvent, at a temperature about 50 to 90° C.;
   2) removing a portion of the solvent;
   3) adding a $C_1$-$C_5$ alcohol; and
   4) cooling to crystallize ziprasidone.

6. The process of claim 1, wherein purifying comprises recrystallizing ziprasidone from a solvent comprising an alcohol, a halogenated solvent, or a mixture thereof.

7. The process of claim 1, wherein purifying comprises recrystallizing ziprasidone from a solvent comprising methanol, ethanol, butanol, or t-butanol.

8. The process of claim 1, wherein purifying comprises recrystallizing ziprasidone from a solvent comprising dichloromethane, chloroform, or carbon tetrachloride.

9. The process of claim 1, wherein purifying comprises recrystallizing ziprasidone from a solvent comprising methanol and chloroform.

10. The process of claim 1, wherein purifying comprises slurrying in a solvent comprising methanol, ethanol, n-butanol, or t-butanol.

11. The process of claim 1, wherein purifying comprises:
    dissolving a mixture of ziprasidone and impurities in a mixture of a $C_1$-$C_5$ alcohol and a halogenated solvent;
    removing a portion of the solvent;
    adding a $C_1$-$C_5$ alcohol; and
    cooling to crystallize ziprasidone.

12. The process of claim 1, wherein purifying comprises slurrying, followed by recrystallization.

13. The process of claim 1, further comprising converting ziprasidone to ziprasidone hydrochloride.

14. The process of claim 13, wherein a product comprises anhydrous ziprasidone hydrochloride.

15. The process of claim 13, wherein a product comprises ziprasidone hydrochloride hemihydrate.

16. The process of claim 13, wherein a product comprises ziprasidone hydrochloride monohydrate.

17. The process of claim 13, further comprising:
    dissolving the ziprasidone hydrochloride in an acid to form a solution;
    cooling the solution;
    adding seed crystals of ziprasidone hydrochloride to the solution; and
    adding an antisolvent to the solution.

18. The process of claim 17, wherein the acid comprises formic acid.

19. The process of claim 17, wherein the antisolvent comprises an ester.

* * * * *